(12) United States Patent
Williamson et al.

(10) Patent No.: US 10,220,548 B2
(45) Date of Patent: Mar. 5, 2019

(54) HUMIDITY ACTIVATED FORMULATION FOR VOLATILE COMPOUNDS

(71) Applicant: AgroFresh, Inc., Collegeville, PA (US)

(72) Inventors: Alexander Williamson, Rosharon, TX (US); Daniel Maclean, Woodland, CA (US)

(73) Assignee: AgroFresh Inc., Philadelphia, PA (US)

( * ) Notice: Subject to any disclaimer, the term of this patent is extended or adjusted under 35 U.S.C. 154(b) by 126 days.

(21) Appl. No.: 14/329,149

(22) Filed: Jul. 11, 2014

(65) Prior Publication Data

US 2015/0018430 A1 Jan. 15, 2015

Related U.S. Application Data

(60) Provisional application No. 61/845,025, filed on Jul. 11, 2013.

(51) Int. Cl.
| | | |
|---|---|---|
| *A61K 36/00* | (2006.01) | |
| *B29C 41/00* | (2006.01) | |
| *B65B 55/04* | (2006.01) | |
| *A23L 3/3463* | (2006.01) | |
| *A01N 25/18* | (2006.01) | |
| *A23B 4/20* | (2006.01) | |
| *A23B 7/154* | (2006.01) | |
| *B29K 29/00* | (2006.01) | |
| *B29L 7/00* | (2006.01) | |
| *B29K 105/00* | (2006.01) | |

(52) U.S. Cl.
CPC ............ *B29C 41/003* (2013.01); *A01N 25/18* (2013.01); *A23B 4/20* (2013.01); *A23B 7/154* (2013.01); *A23L 3/3463* (2013.01); *B65B 55/04* (2013.01); *B29K 2029/04* (2013.01); *B29K 2105/0011* (2013.01); *B29L 2007/008* (2013.01)

(58) Field of Classification Search
None
See application file for complete search history.

(56) References Cited

U.S. PATENT DOCUMENTS

| | | | |
|---|---|---|---|
| 4,715,390 A | 12/1987 | Walt et al. | |
| 4,729,190 A * | 3/1988 | Lee ........................ | A01N 25/10 47/57.6 |
| 6,596,298 B2 * | 7/2003 | Leung ...................... | A23G 3/50 424/405 |
| 2002/0198107 A1 | 12/2002 | Kostansek | |
| 2005/0175805 A1 | 8/2005 | Hild et al. | |
| 2005/0250649 A1 * | 11/2005 | Jacobson ............... | A01N 27/00 504/357 |
| 2006/0013884 A1 | 1/2006 | Il et al. | |
| 2007/0042182 A1 | 2/2007 | Markus et al. | |
| 2008/0220036 A1 * | 9/2008 | Miltz ..................... | A01N 25/10 424/409 |
| 2009/0087468 A1 * | 4/2009 | Stephenson ............ | A01N 25/04 424/408 |
| 2010/0144533 A1 * | 6/2010 | Baier ..................... | A01N 27/00 504/357 |
| 2011/0036367 A1 | 2/2011 | Saito et al. | |
| 2011/0143004 A1 * | 6/2011 | Wood ...................... | A01N 3/00 426/324 |

FOREIGN PATENT DOCUMENTS

| | | | |
|---|---|---|---|
| CN | 102585412 | 7/2012 | |
| JP | 2004-129811 | 4/2004 | |
| JP | 2011-276135 | 12/2011 | |
| WO | 2008089140 A1 | 7/2008 | |
| WO | WO 2008089140 A1 * | 7/2008 | ............ A01N 27/00 |
| WO | 2012/134539 | 10/2012 | |

OTHER PUBLICATIONS

Loo et al. (2008) Food Chemistry 107: 1151-1160.*
Jung (2007) Biotechnology and Bioprocess Engineering 12: 318-322.*
Gilles et al. (2010) Food Chemistry 119: 731-737.*
Mathew et al. (2015) Appl. Microbiol. Biotechnol. 99: 611-622.*
Pauli et al. (2010) Natural Product Communications vol. 5, No. 9, 1387-1394.*
International Search Report and Written Opinion, dated Oct. 16, 2014, pp. 1-13, International Searching Authority, Alexandria, VA.
Mascheroni, Erika et al. "Encapsulation of volatiles in nanofibrous polysaccharide membranes for humidity-triggred release," Carbohydrate Polymers, (Apr. 30, 2013), 98(1): 17-25.

* cited by examiner

*Primary Examiner* — Christopher R Tate
*Assistant Examiner* — Russell G Fiebig
(74) *Attorney, Agent, or Firm* — Barnes & Thornburg LLP

(57) ABSTRACT

This invention is related to controlled release formulations of volatile antimicrobial compounds against pathogens affecting meats, plants, or plant parts or dairy products. Provided are delivery systems in the form of coatings or films, where controlled release of their volatile components in vapor form is triggered by high relative humidity. The volatile component may include, for example volatile antimicrobial liquids including low molecular weight alcohols and/or aldehydes, 1-methylcyclopropene, and/or other volatile fungicides.

10 Claims, No Drawings

HUMIDITY ACTIVATED FORMULATION FOR VOLATILE COMPOUNDS

CROSS REFERENCE

This application claims the benefit of priority under 35 U.S.C. § 119(e) of U.S. Provisional Patent Application No. 61/845,025 filed on Jul. 11, 2013, the content of which is incorporated by reference in its entirety.

BACKGROUND OF THE INVENTION

Existing commercial approaches for delivering volatile antimicrobial oils into a headspace (such as in shoe-boxes) typically involve an absorbent pad, tissue or film which is charged with the volatile oil (by soaking it or exposing it to an atmosphere of the volatile oil) and stored in air-tight packaging before use. One major disadvantage with this approach is that as soon as the pad/tissue/film is removed from its air-tight packaging, as there is little control over the release rate, it may lose a large amount/all of the volatile oil before the release of the volatile oil into the headspace is desired. For example, to use in a supply chain for packaging freshly harvested berries, the material after removal from air-tight packaging, may be exposed to ambient conditions, followed by forced air cooling for several hours, during which time no appreciable release of volatile oil is desired.

Alternative approaches may involve casting coatings from solvents which contain the dissolved volatile oil and a hydrophobic binder. One major disadvantage with this approach is that most of the volatile oil typically escapes from the coating during the drying process, and during storage.

Additional approaches involve the use of beta-cyclodextrin (beta-CD) to encapsulate the volatile oil within a coating. One major disadvantage with beta-CD is its poor solubility in common casting solvents (including water), and its high molecular weight (Mw=1135) relative to the molecular weight of a typical volatile oil. Due to its high molecular weight, a relatively large mass of beta-CD needs to be used to encapsulate the volatile oil, resulting in high expense and relatively low levels of volatile oil incorporated into the coating.

Thus, there remains a need to develop effective material with controlled release of volatile compounds, in particular for agricultural applications.

SUMMARY OF THE INVENTION

This invention is related to controlled release formulations of volatile antimicrobial compounds against pathogens affecting meats, plants, or plant parts or dairy products. Provided are delivery systems in the form of coatings or films, where controlled release of their volatile components in vapor form is triggered by high relative humidity. The volatile component may include, for example volatile antimicrobial liquids including low molecular weight alcohols and/or aldehydes, 1-methylcyclopropene, and/or other volatile fungicides.

In one aspect, provided is a controlled release formulation or humidity-activated material comprising (a) a binder component; and (b) a volatile component dispersed in the binder component.

In one embodiment, the binder component comprises polyvinyl alcohol. In another embodiment, the binder component does not comprise cellulose, starch, gum, or polyethylene glycol (polyethylene oxide).

In one embodiment, the volatile component comprises an antimicrobial compound. In a further embodiment, the antimicrobial compound comprises a volatile fungicide. In another embodiment, the volatile component comprises a volatile oil. In a further embodiment, the volatile oil comprises extracts from an organism selection from the group consisting of *Achillea* spp., *Amomum* spp., *Asteraceae* spp., *Borago* spp., *Brassica* spp., *Bulnesia* spp., *Calamus* spp., *Camellia* spp., *Cananga* spp., *Capsicum* spp., *Cassia* spp., *Cedrus* spp., *Chamaecyparis* spp., *Chrysopogon* spp., *Cinnamomum* spp., *Citrus* spp., *Coriandrum* spp., *Cupressus* spp., *Curcuma* spp., *Cymbopogon* spp., *Dianthus* spp., *Dipterocarpus* spp., *Elettaria* spp., *Eucalyptus* spp., *Forniculum* spp., *Gaultheria* spp., *Geranium* spp., *Glycine* spp., *Gossypium* spp., *Iris* spp., *Jasminear* spp., *Juniperus* spp., *Lavandula* spp., *Linum* spp., *Lippia* spp., *Litsea* spp., *Melaleuca* spp., *Mentha* spp., *Myristica* spp., *Ocimum* spp., *Ornothera* spp., *Origanum* spp., *Pimenta* spp., *Pimpinella* spp., *Pinus* spp., *Piper* spp., *Pogostemon* spp., *Ricinus* spp., *Rosa* spp., *Rosmarinus* spp., *Salvia* spp., *Santalum* spp., *Sassafras* spp., *Secale* spp., *Sesamum* spp., *Simmondsia* spp., *Syringa* spp., *Syzygium* spp., *Thuja* spp., *Thymus* spp., *Trigonella* spp., *Vanilla* spp., *Zea* spp., *Zingiber* spp., and combinations thereof.

In another embodiment, the volatile component does not comprise a substance (for example a gas) with boiling point below zero degree Celsius (0° C.), for example $CO_2$, $ClO_2$ or $SO_2$. In a further embodiment, the volatile component does not comprise $ClO_2$ or $SO_2$. In another embodiment, the volatile component has a boiling point between 40° C. and 300° C. In another embodiment, the volatile component has a boiling point between 100° C. and 300° C. In another embodiment, the volatile component comprises solid or liquid precursors to the volatile compounds (gasses). In another embodiment, the volatile component comprises a volatile compound or a molecular complex of a volatile compound and a molecular encapsulating agent.

In one embodiment, the antimicrobial compound is against a pathogen selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp. In another embodiment, the pathogen is selected from the group consisting of *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp. In another embodiment, the pathogen is selected from the group consisting of *Cryptosporidium* spp. and *Giardia* spp.

In another embodiment, the package material is for use for meats, plants, plant parts, and/or dairy products. In a further embodiment, the plants or plant parts comprise transgenic plants or transgenic plant parts. In another embodiment, the plants or plant parts are selected from the group consisting of barley, camphor tree, canola, castor-oil plant, cinnamon, cocoa, coffee, corn, cotton, flax, grapevine, hemp, hops, jute, maize, mustard, nuts, oat, poppy, rape, rice, rubber plant, rye, sunflower, sorghum, soybean, sugar cane, tea, tobacco, and wheat. In another embodiment, the plants or plant parts are selected from the group consisting of fruit, vegetables, nursery, turf and ornamental crops. In a further embodiment, the fruit is selected from the group consisting of almond, apple, avocado, banana, berries (including strawberry, blueberry, raspberry, blackberry, currents and other types of berries), carambola, cherry, citrus (including oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. In a further embodiment, the vegetable is selected from the group consisting of asparagus, beet (including sugar and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (sweet, bell or hot), potato, pumpkin, sweet potato, snap bean, squash, tomato and turnip. In a further embodiment, the nursery plant or flower or flower part is selected from the group consisting of roses, carnation, geranium, gerbera, lily, orchid, or other cut-flowers or ornamental flowers, flower bulbs, shrub, deciduous or coniferous tree. In a further embodiment, the meat is selected from the group of beef, bison, chicken, deer, goat, turkey, pork, sheep, fish, shellfish, mollusks, or dry-cured meat products.

In another embodiment, the volatile compound comprises a cyclopropene compound of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl. In another embodiment, the volatile compound comprises a cyclopropene compound of the formula:

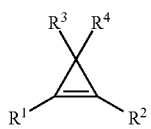

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or naphthyl group; and $R^2$, $R^3$, and $R^4$ are hydrogen.

In another embodiment, the volatile compound comprises 1-methylcyclopropene (1-MCP). In a further embodiment, the package material comprises between 0.01% and 30%; between 0.1% and 10%; between 0.3% and 3%; or between 10% and 25% of 1-MCP.

In another embodiment, the molecular encapsulating agent is selected from the group consisting of alpha-cyclodextrin, beta-cyclodextrin, gamma-cyclodextrin, or combinations thereof. In another embodiment, the molecular encapsulating agent comprises alpha-cyclodextrin or beta-cyclodextrin. In a further embodiment, the molecular encapsulating agent comprises beta-cyclodextrin. In another embodiment, the volatile component is not substantially released below 30% relative humidity after a period of five (5) hours, but is released between 60% and 100%; between 75% and 100%; or between 80% and 90% relative humidity at room temperature.

In another aspect, provided is a method for preparing the controlled release material. The method comprises (a) dispersing the volatile component in an aqueous solution or dispersion of a binder component to form a mixture; and (b) casting the mixture onto a package material. In another embodiment, the mixture may be cast onto a substrate to give a coated sheet which may be inserted into, onto, beneath, or adjacent to a packaging material. In another embodiment, the coating may be peeled off the coated sheet to give a film which may be inserted into, onto, beneath, or adjacent to a packaging material.

In one embodiment, no radiation is used. In another embodiment, the binder component comprises polyvinyl alcohol. In another embodiment, the binder component does not comprise cellulose, starch, gum, polyethylene oxide, or polyethylene glycol.

In one embodiment, the volatile component comprises an antimicrobial compound. In a further embodiment, the antimicrobial compound comprises a volatile fungicide. In another embodiment, the volatile component comprises a volatile oil. In a further embodiment, the volatile oil comprises extracts from an organism selection from the group consisting of *Achillea* spp., *Amomum* spp., *Asteraceae* spp., *Borago* spp., *Brassica* spp., *Bulnesia* spp., *Calamus* spp., *Camellia* spp., *Cananga* spp., *Capsicum* spp., *Cassia* spp., *Cedrus* spp., *Chamaecyparis* spp., *Chrysopogon* spp., *Cinnamomum* spp., *Citrus* spp., *Coriandrum* spp., *Cupressus* spp., *Curcuma* spp., *Cymbopogon* spp., *Dianthus* spp., *Dipterocarpus* spp., *Elettaria* spp., *Eucalyptus* spp., *Forniculum* spp., *Gaultheria* spp., *Geranium* spp., *Glycine* spp., *Gossypium* spp., *Iris* spp., *Jasminear* spp., *Juniperus* spp., *Lavandula* spp., *Linum* spp., *Lippia* spp., *Litsea* spp., *Melaleuca* spp., *Mentha* spp., *Myristica* spp., *Ocimum* spp., *Ornothera* spp., *Origanum* spp., *Pimenta* spp., *Pimpinella* spp., *Pinus* spp., *Piper* spp., *Pogostemon* spp., *Ricinus* spp., *Rosa* spp., *Rosmarinus* spp., *Salvia* spp., *Santalum* spp., *Sassafras* spp., *Secale* spp., *Sesamum* spp., *Simmondsia* spp., *Syringa* spp., *Syzygium* spp., *Thuja* spp., *Thymus* spp., *Trigonella* spp., *Vanilla* spp., *Zea* spp., *Zingiber* spp., and combinations thereof.

In another embodiment, the volatile component does not comprise a substance (for example a gas) with boiling point below zero degree Celsius (0° C.), for example $CO_2$, $ClO_2$ or $SO_2$. In a further embodiment, the volatile component does not comprise $ClO_2$ or $SO_2$. In another embodiment, the volatile component has a boiling point between 40° C. and 300° C. In another embodiment, the volatile component has a boiling point between 100° C. and 300° C. In another embodiment, the volatile component comprises solid or liquid precursors to the volatile compounds (gasses). In another embodiment, the volatile component comprises a volatile compound or a molecular complex of a volatile compound and a molecular encapsulating agent.

In one embodiment, the antimicrobial compound is against a pathogen selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp. In another embodiment, the pathogen is selected from the group consisting of *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp. In another embodiment, the pathogen is selected from the group consisting of *Cryptosporidium* spp. and *Giardia* spp.

In another embodiment, the material is for use for meats, plants, plant parts, and/or dairy products. In a further embodiment, the plants or plant parts comprise transgenic plants or transgenic plant parts. In another embodiment, the plants or plant parts are selected from the group consisting of barley, camphor tree, canola, castor-oil plant, cinnamon, cocoa, coffee, corn, cotton, flax, grapevine, hemp, hops, jute, maize, mustard, nuts, oat, poppy, rape, rice, rubber plant, rye, sunflower, sorghum, soybean, sugar cane, tea, tobacco, and wheat. In another embodiment, the plants or plant parts are selected from the group consisting of fruit, vegetables, nursery, turf and ornamental crops. In a further embodiment, the fruit is selected from the group consisting of almond, apple, avocado, banana, berries (including strawberry, blueberry, raspberry, blackberry, currents and other types of berries), carambola, cherry, citrus (including oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. In a further embodiment, the vegetable is selected from the group consisting of asparagus, beet (including sugar and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (sweet, bell or hot), potato, pumpkin, sweet potato, snap bean, squash, tomato and turnip. In a further embodiment, the nursery plant or flower or flower part is selected from the group consisting of roses, carnation, geranium, gerbera, lily, orchid, or other cut-flowers or ornamental flowers, flower bulbs, shrub, deciduous or coniferous tree. In a further embodiment, the meat is selected from the group of beef, bison, chicken, deer, goat, turkey, pork, sheep, fish, shellfish, mollusks, or dry-cured meat products.

In another embodiment, the volatile compound comprises a cyclopropene compound of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl. In another embodiment, the volatile compound comprises a cyclopropene compound of the formula:

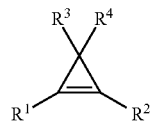

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or naphthyl group; and $R^2$, $R^3$, and $R^4$ are hydrogen.

In another embodiment, the volatile compound comprises 1-methylcyclopropene (1-MCP). In a further embodiment, the package material comprises between 0.1% and 10%; between 0.3% and 3%; or between 0.01% and 1% of the 1-MCP.

In another embodiment, the molecular encapsulating agent is selected from the group consisting of alpha-cyclodextrin, beta-cyclodextrin, gamma-cyclodextrin, or combinations thereof. In another embodiment, the molecular encapsulating agent comprises alpha-cyclodextrin or beta-cyclodextrin. In a further embodiment, the molecular encapsulating agent comprises beta-cyclodextrin. In another embodiment, the volatile component is not substantially released below 30% relative humidity after five (5) hours, but is released between 60% and 100%; between 75% and 100%; or between 80% and 100% relative humidity at room temperature.

In some embodiments, the mixture has a viscosity greater than 100 cPs (centipoise); or greater than 500 cPs. In other embodiment, the mixture has a viscosity between 100 and 50,000 cPs; between 250 and 30,000 cPs; between 500 and 30,000 cPs; or between 500 and 50,000 cPs.

In another aspect, provided is a method for preparing the material provided herein. The method comprises (a) dispersing the volatile component in an aqueous solution or dispersion of a binder component; (b) casting the mixture onto a solid substrate; and (c) solidifying the mixture to generate a coating on the solid substrate.

In one embodiment, no radiation is used. In another embodiment, the solidifying step comprises drying with heat. In a further embodiment, the heat is applied at a temperature between 10° C. and 120° C.; between 15° C. and 100° C.; or between 20° C. and 110° C. In another embodiment, the heat is applied at a temperature between 40° C. and 120° C.; between 60° C. and 100° C.; or between 80° C. and 110° C.

In another embodiment, the solidifying step comprises drying with a stream of gas (for example air). In a further embodiment, the stream of gas is applied at a temperature between 10° C. and 120° C.; between 15° C. and 100° C.; or between 20° C. and 110° C. In another embodiment, the stream of gas is applied at a temperature between 40° C. and 120° C.; between 60° C. and 100° C.; or between 80° C. and 110° C.

In some embodiments, the mixture has a viscosity greater than 100 cPs (centipoise); or greater than 500 cPs. In other embodiment, the mixture has a viscosity between 100 and 50,000 cPs; between 250 and 30,000 cPs; between 500 and 30,000 cPs; or between 500 and 50,000 cPs.

In some embodiments, the mixture has a viscosity greater than 90 cPs; greater than 100 cPs; greater than 250 cPs; or greater than 500 cPs. In other embodiment, the mixture has a viscosity between 50 and 2,000 cPs; between 90 and 100 cPs; or between 250 and 1,000 cPs.

In another aspect, provided is a method for preparing the material provided herein. The method comprises (a) preparing a first liquid comprising the binder; (b) mixing the first liquid with the volatile component to generate a mixture; (c) casting the mixture onto a solid substrate; and (d) solidifying the mixture to generate the package material.

In one embodiment, no radiation is used. In another embodiment, the solidifying step comprises drying with heat. In a further embodiment, the heat is applied at a temperature between 10° C. and 120° C.; between 15° C. and 100° C.; or between 20° C. and 110° C. In another embodiment, the heat is applied at a temperature between 40° C. and 120° C.; between 60° C. and 100° C.; or between 80° C. and 110° C.

In another embodiment, the solidifying step comprises drying with a stream of gas (for example air). In a further embodiment, the stream of gas is applied at a temperature between 10° C. and 120° C.; between 15° C. and 100° C.; or between 20° C. and 110° C. In another embodiment, the stream of gas is applied at a temperature between 40° C. and 120° C.; between 60° C. and 100° C.; or between 80° C. and 110° C.

In some embodiments, the mixture has a viscosity greater than 100 cPs (centipoise); or greater than 500 cPs. In other embodiment, the mixture has a viscosity between 100 and 50,000 cPs; between 250 and 30,000 cPs; between 500 and 30,000 cPs; or between 500 and 50,000 cPs.

In some embodiments, the mixture has a viscosity greater than 90 cPs; greater than 100 cPs; greater than 250 cPs; or greater than 500 cPs. In other embodiment, the mixture has a viscosity between 50 and 2,000 cPs; between 90 and 100 cPs; or between 250 and 1,000 cPs.

In another aspect, provided is a material which is in the form of a coating on a packaging material. In another aspect, provided is a material which is in the form of a sheet which is inserted into, onto, beneath, or adjacent to a packaging material. In another aspect, provided is a material which is in the form of a label which is adhered onto a packaging material. In another aspect, provided is a method of applying the material provided herein. The method comprises (a) inserting fresh produce into a package; (b) inserting the coated substrate, film, sheet, or label into, onto, beneath, or adjacent to the package; and (c) sealing or enclosing the package, thereby the material is exposed to high relative humidity generated by the fresh produce.

DETAILED DESCRIPTION OF THE INVENTION

The controlled release formulation/material/delivery system provided herein may include a volatile (liquid) component encapsulated within a film or coating. In one embodiment, the film or coating has the following advantages: (1) retaining/encapsulating the volatile (liquid) component under dry conditions or conditions of moderate relative humidity (even when heated), and (2) releasing the volatile (liquid) component (in vapor form) on exposure to high relative humidity or moisture.

The controlled release formulation/material/delivery system in the form of a coating or film provided herein uses a binder which is a good barrier to organic gasses at low/moderate relative humidity, resulting in little/no diffusion of the volatile component (for example volatile oil) out of the coating or film under typical ambient conditions. The high relative humidity inside fruit, vegetable, ornamental flower, meat, or cheese packaging (typically 90%+) is used as a trigger to release the volatile component (for example volatile oil). The rate of release at high humidity can be adjusted by adjustment of the coating formulation.

The embodiments provided provide the advantage to avoid substantial loss of the volatile component (for example volatile oil) during the drying process by use of a binder which is a good barrier to organic gasses at low/moderate relative humidity. In one embodiment, during the drying process, a skin (or top surface) is first formed on the surface of the coating. The skin (or top surface) is impermeable to the volatile component (for example volatile oil), but permeable to water vapor. Hence the remainder of the water evaporates from the coating but the volatile component (for example volatile oil) remains trapped inside.

Suitable compounds for the volatile component include aliphatic or aromatic compounds, including their acids, alcohols, aldehydes, esters, and ketones. In another embodiment, the compound is a monoterpenoid or aliphatic structure up to 12 carbons in length. In a further embodiment, the compound is selected from the group consisting of allyl disulfide, allyl sulfide, amyl cinnamic aldehyde, α-phellandrene, amyl cinnamic aldehyde, amyl salicylate, anethole, trans-anethole, anisic aldehyde, p-anisaldehyde, benzaldehyde, benzyl acetate, benzyl alcohol, bergamot, bicyclogermacrene, borneol, bornyl acetate, 2-butene, α-butylene, D-cadinene, calamenene, α-campholenic aldehyde, camphor, χ-caryophyllene, caryophyllene oxide, trans-caryophyllene, carvacrol, carveol, 4-carvomenthenol, carvone, cineole, 1,4-cineole, 1,8-cineole, cinnamaldehyde, hexyl-cinnamaldehyde, trans-cinnamaldehyde, cinnamic alcohol, α-cinnamic terpinene, α-isoamyl-cinnamic, cinnamyl alcohol, citral, citric acid, citronella and oil, citronellal, hydroxy citronellal, citronellol, α-citronellol, citronellyl acetate, citronellyl nitrile, corn gluten meal, coumarin, cuminaldehyde, p-cymene, decanal, trans-2-decenal, decyl aldehyde, diethyl phthalate, dihydroanethole, dihydrocarveol, dihydrocarvone, dihydrolinalool, dihydromyrcene, dihydromyrcenol, dihydromyrcenyl acetate, dihydroterpineol, dill, dimethyl salicylate, cis-3,7-dimethyl-1,6-octadien-3yl acetate, cis-3,7-dimethyl-2,6-octadien-1-ol, dimethyloctanal, dimethyloctanol, dimethyloctanyl acetate, dimethyl salicylate, dimethyl thiophene, diphenyl oxide, dipropylene glycol, dodecanal, estragole, ethyl vanillin, eucalyptol, eugenol, eugenyl acetate, farnesol, fenchol, ferniol, furfural, galaxolide, geraniol, geranyl acetate, geranyl nitrile, globulol, guaiacol, gurjunene, heliotropin, herbanate, 1-hexanol, hexanal, trans-2-hexen-1-al, α-humulene, hydrogen peroxide, ionone, isoamyl isovalerate, isobutyl quinoleine, isobornyl acetate, isobornyl methylether, isobutyric anhydride, isoeugenol, isolongifolene, isosafrole, isothiocyanate, jasmonic acid, lauryl sulfate, lavandin, limonene, linalool oxide, linalool, linalyl acetate, longifolene, malic acid, menthe, menthane hydroperoxide, menthol, menthyl acetate, menthofurane, menthol, menthone, methional, methyl acetate, methyl anthranilate, methyl cedryl ketone, methyl chavicol, methyl cinnamate, methyl cyclopropane, methyl eugenol, methyl hexyl ether, methyl ionone, methyl jasmonate, 1-methyl-4-isopropyl-1-cyclohexen-8-ol, methyl salicylate, 3-methyl thiopropionaldehyde, muscone, musk xylol, myrcene, neral, nerol, neryl acetate, nonyl aldehyde, trans-β-ocimene, palustrol, perillaldehyde, petitgrain, α-phellandrene, p-hydroxy phenyl butanone, phenyl ethyl alcohol, phenyl ethyl propionate, phenyl ethyl-2-methylbutyrate, cis-pinane, pinane hydroperoxide, pinanol, pine ester, α-pinene, α-pinene oxide, β-pinene, piperonal, piperonyl acetate, piperonyl alcohol, plinol, plinyl acetate, potassium sorbate, 2-propanol, 2-propenyl methyl disulphide, 1-proponyl methyl disulphide, pseudoionone, pulegone, rhodinol, rhodinyl acetate, rosalin, rosemarinic acid, safrole, salicylaldehyde, sandenol, sodium chloride, sodium lauryl sulfate, sotolon, spathulenol, spirantol, terpenoid, terpineol, α-terpineol, terpine-4-ol, α-terpinene, λ-terpinene, terpinolene, terpinyl acetate, tert-butylcyclohexyl acetate, tetrahydrolinalool, tetrahydrolinalyl acetate, tetrahydromyrcenol, α,β-thujone, thymol, turpentine, undecanoic acid, 10-undecenoic acid, vanillin, and verbenone.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg, *Advanced Organic Chemistry* 4$^{th}$ Ed., Vols. A (2000) and B (2001), Plenum Press, New York, N.Y.

The term "composition," as used herein, includes a mixture of materials which comprise the composition, as well as reaction products and decomposition products formed from the materials of the composition.

Embodiments provided herein may include one or more polymer(s) listed herein.

The term "humidity-activated," as used herein, refers to that the volatile component is released as a vapor on exposure of the material to high humidity. In one embodiment, high humidity includes 75% to 100% relative humidity. In another embodiment, high humidity includes 60% to 100% relative humidity.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer.

The term "functionalized polymer," as used herein, refers to a polymer that comprises, linked by a covalent bond, a chemical group (chemical substituent) comprising at least one heteroatom. A heteroatom is defined as an atom which is not carbon or hydrogen. Common heteroatoms are oxygen, nitrogen, sulfur, and phosphorus.

The term "functional group," as used herein, refers to a chemical substituent containing at least one heteroatom. A heteroatom is defined as an atom which is not carbon or hydrogen. Common heteroatoms include oxygen, nitrogen, sulfur, and phosphorus.

The term "perishable material," as used herein, refers to organic matter which can spoil or decay, or which has a decrease in activity of one or more of its active components over time.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The practice of the present invention may involve the use of one or more cyclopropene compounds. As used herein, a cyclopropene compound is any compound with the formula

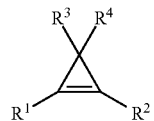

where each $R^1$, $R^2$, $R^3$ and $R^4$ is independently selected from the group consisting of H and a chemical group of the formula:

where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$, and $R^4$ groups are independently selected from the suitable groups. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted.

Among the suitable $R^1$, $R^2$, $R^3$, and $R^4$ groups are, for example, aliphatic groups. Some suitable aliphatic groups include, for example, alkyl, alkenyl, and alkynyl groups.

Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent.

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl, butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and naphthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In one embodiment, one or more of $R^1$, $R^2$, $R^3$, and $R^4$ is hydrogen or $(C_1-C_{10})$ alkyl. In another embodiment, each of $R^1$, $R^2$, $R^3$, and $R^4$ is hydrogen or $(C_1-C_8)$ alkyl. In another embodiment, each of $R^1$, $R^2$, $R^3$, and $R^4$ is hydrogen or $(C_1-C_4)$ alkyl. In another embodiment, each of $R^1$, $R^2$, $R^3$, and $R^4$ is hydrogen or methyl. In another embodiment, $R^1$ is $(C_1-C_4)$ alkyl and each of $R^2$, $R^3$, and $R^4$ is hydrogen. In another embodiment, $R^1$ is methyl and each of $R^2$, $R^3$, and $R^4$ is hydrogen, and the cyclopropene compound is known herein as 1-methylcyclopropene or "1-MCP."

In another embodiment, the cyclopropene is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy. In one embodiment, R is $C_{1-8}$ alkyl. In another embodiment, R is methyl.

In another embodiment, the cyclopropene is of the formula:

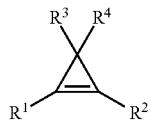

wherein $R^1$ is a substituted or unsubstituted $C_1-C_4$ alkyl, $C_1-C_4$ alkenyl, $C_1-C_4$ alkynyl, $C_1-C_4$ cycloalkyl, cycloalkylalkyl, phenyl, or naphthyl group; and $R^2$, $R^3$, and $R^4$ are hydrogen. In another embodiment, the cyclopropene comprises 1-methylcyclopropene (1-MCP).

As used herein, the phrase "transgene vector" refers to a vector that contains an inserted segment of DNA, the "transgene" that is transcribed into mRNA or replicated as RNA within a host cell. The phrase "transgene" refers not only to that portion of inserted DNA that is converted into RNA, but also those portions of the vector that are necessary for the transcription or replication of the RNA. A transgene typically comprises a gene-of-interest but needs not necessarily comprise a polynucleotide sequence that contains an open reading frame capable of producing a protein.

Meats, plants, or plant parts, or dairy products may be treated in the practice of the present invention. One example is treatment of whole plants; another example is treatment of whole plants while they are planted in soil, prior to the harvesting of useful plant parts.

Any plants that provide useful plant parts may be treated in the practice of the present invention. Examples include plants that provide fruits, vegetables, nursery crops, flowers and grains.

As used herein, the phrase "plant" includes dicotyledons plants and monocotyledons plants. Examples of dicotyledons plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale. Examples of fruit include apple, avocado, banana, berries (including strawberry, blueberry, raspberry, blackberry, currents and other types of berries), carambola, cherry, citrus (including oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. Examples of vegetable include asparagus, beet (including sugar and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (sweet, bell or hot), potato, pumpkin, sweet potato, snap bean, squash, tomato and turnip. Examples of nursery plant or flower or flower part include roses, carnation, geranium, gerbera, lily, orchid, or other cut-flowers or ornamental flowers, flower bulbs, shrub, deciduous or coniferous tree Various embodiments provided are based on dispersion of the volatile (liquid) component in a binder which is a good barrier to organic gasses under conditions of low/moderate relative humidity, but a poor barrier to organic gasses under conditions of high relative humidity.

In one embodiment, the volatile (liquid) component comprises an essential oil/natural oil/plant extract with antimicrobial properties. In another embodiment, the film/coating provided herein can be inserted inside packaging for fruit, vegetable, flower, or other plant parts, meat or cheese, to control mold or bacterial growth. Various volatile essential oils/natural oils/plant extracts (referred to henceforth as "volatile oils") are known to delay the onset of mold growth and are currently used commercially in packaging applications.

Suitable binders include water-soluble or water-dispersible binders for example polyvinyl alcohol (PVOH), where polyvinyl alcohol refers to fully or partially hydrolyzed polyvinyl acetate, polyvinylpyrrolidone, polyvinylpyridine, polyvinylimidazole, polyvinylcaprolactam, polyethylene glycol, polypropylene glycol, functionalized cellulose such as cellulose containing methoxy functions, or hydroxyethyl or hydroxypropyl functions, polyhydroxyethyl(meth)acrylate, polyethyleneimine, polyethylene-co-acrylic acid or salts thereof, poly(meth)acrylic acid or salts thereof, polystyrene sulfonic acid or salts thereof, polyethylene-co-vinyl alcohol (EVOH), or gums for example acacia gum. Copolymers of these polymers with other monomeric units may be suitable binders as well.

A suitable binder for various embodiments provided herein includes polyvinyl alcohol, as it is a good barrier to organic gasses when dry and a poor barrier when exposed to high relative humidity. In one embodiment, polyvinyl alcohol is used with a hydrolysis degree between 55% and 100%; or between 65% and 99%.

Suitable volatile oils for various embodiments provided herein include non-water-soluble liquid substances which can form (with optional aid of a dispersant) a stable emulsion in an aqueous solution of the binder.

As used herein, a fluid is "non-aqueous" if it contains, by weight based on the weight of the fluid, 10% water or less. As used herein, a liquid that has high viscosity is a composition that is liquid at 25° C. and that has viscosity at 25° C. at shear rate of 0.01 sec$^{-1}$ of 10 Pa*s (10 Poise) or more.

The solution provided may have a viscosity of from about 100 to about 50,000 centiPoise; or 500 to 30,000 centiPoise. Below the preferred viscosity, the dispersed oil droplets are thought to migrate rapidly to the surface of the coating while drying and hence escape to the atmosphere during the drying process. In another preferred embodiment, the coating is dried under a stream of gas, preferably air, in order to rapidly form an impermeable skin on the surface of the coating.

Various embodiments provided herein are in the form of a sheet (coated substrate or free-standing film) or a label, which is inserted into a package or a pallet, or a coating on the inside or outside surface of the packaging material. The package can be a small consumer-size package, a bulk bag, a box, or a pallet wrap.

Those skilled in the art would understand certain variation can exist based on the disclosure provided. Thus, the following examples are given for the purpose of illustrating the invention and shall not be construed as being a limitation on the scope of the invention or claims.

EXAMPLES

Example 1

25 grams polyvinyl alcohol (Mowiol 4-88, degree of hydrolysis 88%) is dissolved in 75 grams deionized water under stirring and gentle warming, to generate solution A1, which is allowed to cool to ambient.

0.042 gram sodium dodecyl sulphate is dissolved in 3.57 grams deionized water, and 8.33 grams 1-hexanol is added drop-wise while stirring rapidly with a magnetic stirrer to generate emulsion B1. The white emulsion B1 is added to solution A1 and then shaken to produce a white mixture C1, where mixture C1 has a viscosity of about 983 cPs (shear rate=2.31 s$^{-1}$). The amount of 1-hexanol relative to the total amount of [PVOH+1-hexanol] is 25% by weight.

The white mixture C1 is cast onto a PET substrate at a wet thickness of 254 microns, and then dried to produce Formulation D1.

TABLE 1

Headspace analysis of Formulation D1 (25% PVOH, high viscosity).

| Formulation D1 | Drying conditions | % RH in vial | Area of film strip (cm$^2$) | ppm 1-hexanol in 20 mL headspace |
|---|---|---|---|---|
| Sample 1-1 (comparative) | Ambient, 16 hours | Ambient* 100% | 16 15.3 | 0 2 |
| Sample 1-2 | Cool air stream 15 minutes, then ambient 16 hours | Ambient* 100% | 14.3 15.4 | 0 592 |

*Ambient % RH is 49% when the GC samples are prepared

The dried [PVOH/1-hexanol/sds] coatings on PET are cut into strips of approximately 15 cm$^2$ and then the coatings are peeled off the PET strips and the delaminated coating strips placed in an oven at 80° C. for 15 minutes in order to remove any remaining non-encapsulated 1-hexanol.

The strips of coating are then placed inside GC headspace vials (20 mL). In some cases a droplet of water (0.10 mL) is added to the bottom of the vial (avoiding contact with the strip) before the vial is sealed, in order to generate an atmosphere of 100% relative humidity (RH). The vials are then allowed to equilibrate for at least 10 hours before placing in an Agilent GC for analysis of the concentration of 1-hexanol in the headspace. A vial containing pure 1-hexanol (0.50 mL) is used as reference. The reference vial is assumed to create a saturated concentration of 1224 ppm of 1-hexanol in the headspace (calculated from known vapor pressure of 0.124 kPa at 25° C.).

The concentrations of 1-hexanol detected in the headspaces of the vials from Formulation D1 are shown in Table 1. It can be seen that the sample which is dried under a stream of air and also exposed to 100% humidity releases a significant amount of 1-hexanol into the headspace.

Example 2

15 grams polyvinyl alcohol (Mowiol 4-88, degree of hydrolysis 88%) is dissolved in 85 grams deionized water under stirring and gentle warming, to generate solution A2, which is allowed to cool to ambient.

TABLE 2

Headspace analysis of Formulation
D2 (15% PVOH, low viscosity).

| Formulation D2 | Drying conditions | % RH in vial | Area of film strip (cm$^2$) | ppm 1-hexanol in 20 mL headspace |
|---|---|---|---|---|
| Sample 2-1 (comparative) | Ambient, 16 hours | Ambient* 100% | 15.1 14.3 | 0 0 |
| Sample 2-2 (comparative) | Cool air stream 15 minutes, then ambient 16 hours | Ambient* 100% | 14.3 14.2 | 0 0 |

*Ambient % RH is 49% when the GC samples are prepared 0.025 grams sodium dodecyl sulphate is dissolved in 2.14 grams deionized water, and 5 grams 1-hexanol is added drop-wise while stirring rapidly with a magnetic stirrer to generate emulsion B2. The white emulsion B2 is added to solution A2 and then shaken to produce a white mixture C2, where mixture C2 has a viscosity of about 94 cPs (shear rate=26.4 s$^{-1}$). The amount of 1-hexanol relative to the total amount of [PVOH+1-hexanol] is 25% by weight.

The white mixture C2 is cast onto a PET substrate at a wet thickness of 254 microns, and dried according to produce Formulation D2.

A similar headspace analysis as in Example 1 is performed, and 1-hexanol detected in the headspaces of the vials from Formulation D2 are shown in Table 2.

Results from Examples 1 and 2 indicate that a combination of relatively high viscosity coating solution and drying under a stream of air is needed in order to encapsulate the 1-hexanol inside the PVOH film. In addition, 1-hexanol is not released under ambient relative humidity, but significant amounts are released at about or close to 100% relative humidity at ambient temperature (20-25° C.).

Example 3

A mixture C3 is made and cast onto a PET substrate to produce Formulation D3 [PVOH/1-hexanol/sds] in a similar manner as in Example 1, except a stronger air-stream was used for drying the coatings than in Examples 1 and 2. The dried coating on PET is cut into strips of approximately 7 cm$^2$ and then the coating is peeled off each strip and placed in an oven at 80° C. for 15 minutes in order to remove any non-encapsulated 1-hexanol. The delaminated strips of coating are then placed inside GC headspace vials. The GC headspace vials contained small vessels containing different saturated salt solutions (about 0.15 mL) in order to control the relative humidity inside the GC vials. The theoretical relative humidities generated by the saturated aqueous salt solutions at 20° C. are shown in Table 3. The salts used to generate the different relative humidities are: LiCl gives 11% RH; MgCl$_2$ gives 33% RH; K$_2$CO$_3$ gives 43% RH; Mg(NO$_3$)$_2$ gives 54% RH; NaBr gives 58% RH (at 25° C.); KI gives 69% RH (at 25° C.); NaCl gives 76% RH; and K$_2$SO$_4$ gives 98% RH. The vials are left to stand at 20° C. for 13-17 hours, and then the concentration of 1-hexanol in the headspace is analyzed by Agilent GC. Mixture C3 also has a viscosity of about 983 cPs.

TABLE 3

Headspace analysis for Formulation
D3 (25% PVOH, high viscosity).

| Drying Conditions | % RH in GC vial (20° C.) | Area of film strip (cm$^2$) | ppm 1-hexanol in 20 mL headspace after 13-17 hours |
|---|---|---|---|
| Cool air stream 15 minutes, then ambient 16 hours | 11% | 6.9 | 11 |
| | 33% | 6.79 | 59 |
| | 43% | 7.13 | 395 |
| | 54% | 6.9 | 587 |
| | 58% (25° C.) | 6.9 | 1055 |
| | 69% (25° C.) | 6.9 | 1143 |
| | 76% | 6.9 | 1128 |
| | 98% | 6.86 | 1062 |

A vial containing pure 1-hexanol (0.50 mL) is used as reference. The reference vial is assumed to create a saturated concentration of 1224 ppm of 1-hexanol in the headspace (calculated from known vapor pressure of 0.124 kPa at 25° C.). The concentrations of 1-hexanol found in the headspaces of the vials for Formulation D3 are shown in Table 3.

The results show that after 13-17 hours, greater amounts of 1-hexanol have been released corresponding to increasing degrees of relative humidity inside the GC headspace vials at ambient temperature (20-25° C.).

Example 4

A mixture C4 is made and cast onto a PET substrate to produce Formulation D3 [PVOH/1-hexanol/sds] in a similar manner as in Example 1, except a stronger air-stream was used for drying the coatings than in Examples 1 and 2. The dried coating on PET is cut into strips of approximately 7 cm$^2$ and then the coating is peeled off each strip and placed in an oven at 80° C. for 15 minutes in order to remove any non-encapsulated 1-hexanol. The delaminated strips of coating are then placed inside GC headspace vials. The GC headspace vials contained small vessels containing saturated aqueous solutions of KNO$_3$ (about 1.5 mL) which theoretically generated an atmosphere of 95% relative humidity inside the vials. At different intervals after sealing the strip of coating inside the GC vial, headspace samples are injected into the Agilent GC for analysis of concentration of 1-hexanol.

TABLE 4

Headspace analysis for Formulation
D4 (25% PVOH, high viscosity).

| Drying Conditions | Time elapsed after sealing GC vial (hrs) | Area of film strip (cm$^2$) | ppm 1-hexanol in 20 mL headspace |
|---|---|---|---|
| Cool air stream 15 minutes, then ambient 16 hours | 0.15 | 6.49 | 54 |
| | 0.63 | 6.6 | 278 |
| | 1.18 | 6.75 | 650 |
| | 1.73 | 6.6 | 863 |
| | 2.25 | 6.79 | 961 |
| | 2.78 | 6.9 | 964 |
| | 3.33 | 6.9 | 1043 |
| | 4.43 | 6.75 | 1057 |
| | 8.82 | 7.05 | 1098 |

A vial containing pure 1-hexanol (0.50 mL) is used as reference. The reference vial was assumed to create a saturated concentration of 1224 ppm of 1-hexanol in the headspace (calculated from known vapor pressure of 0.124 kPa at 25° C.). The results of headspace analysis are shown in Table 4, indicating the rapid rate of release of 1-hexanol from the delaminated strip of coating at a relative humidity of 95% at ambient temperature (20-25° C.). Mixture C4 also has a viscosity of about 983 cPs (shear rate=2.31 s$^{-1}$).

Example 5

Comparison of 1-Hexanol, trans-2-hexenal, and Guaiacol

Preparation of PVOH Emulsions containing 1-Hexanol, trans-2-hexenal, or guaiacol: 35.0 g Poly vinyl alcohol (PVOH, Mowiol 4-88) is added to a glass beaker and then 65.0 g filtered de-ionized (DI) water is added. The mixture is heated to 60-80° C. and stirred with a mechanical stirrer until the PVOH is fully dissolved. Aluminum foil is used to cover the beaker to reduce evaporation during heating—the beaker is weighed before heating and after dissolution of the PVOH, and additional DI water is added to replace any water lost due to evaporation.

0.0583 g sodium dodecyl sulfate (SDS) is added into 5.0 g DI water. The mixture is stirred on a magnetic stirrer until the SDS is dissolved. To the solution of SDS in water is added 11.667 g 1-hexanol, trans-2-hexenal, or guaiacol (the "actives") drop-wise, under rapid stirring to form a white emulsion (70 weight % 1-hexanol, trans-2-hexenal, or guaiacol in water). The resultant emulsion is then added to the cooled solution of PVOH in the beaker and the resultant mixture stirred mechanically for 5 minutes. In the case of 1-hexanol, and trans-2-hexenal, the resultant homogeneous white emulsion is allowed to stand for approximately hours to allow bubbles to dissipate before casting. In the case of guaiacol, a transparent solution is obtained.

Casting of Emulsions: Using an Elcometer 4340 film applicator with a Gardco Microm II film 9" casting blade, the [PVOH/1-hexanol/SDS/water] emulsion, the [PVOH/trans-2-hexenal/SDS/water] emulsion, or the [PVOH/guaiacol/SDS/water] solution, is cast onto a PET sheet. A wet thickness of 10 mils (254 microns) is used. Immediately after casting, the coating is dried using a commercial hair-dryer directed at an angle of approximately 45° to the plane of the coating, on low-speed, cool setting, for 15 minutes. The coating is then left on a drying rack in the fume-hood overnight.

Quantification of Amount of 1-hexanol, trans-2-hexenal or guaiacol in Coating: A strip of approximately 6.8 cm$^2$ is cut from the middle of the coated PET sheet. The coating is peeled off the PET backer and then placed in a petri-dish in a fume-hood overnight to allow any residual non-encapsulated active to evaporate. The following day, the delaminated coating is precisely weighed into a 20 mL GC vial. 5.0 grams of DI water is added, and the vial immediately sealed. The contents of the vial are gently swirled to dissolve the coating in the water, and at least 10 hours are allowed for the headspace to equilibrate with the aqueous phase. A headspace sample is then removed by syringe for injection into the GC column. Quantification of active is done by comparing to a calibration curve of "GC Peak Area of Headspace sample" vs. "Concentration of 1-hexanol, trans-2-hexenal, or guaiacol in solution" generated with samples of known concentrations of active compound dissolved in DI water in GC vials (after leaving at least 10 hours for equilibration).

TABLE 5

Quantification of compounds using GC analysis

| Active Compound | % Incorporated active (compared to theoretical maximum amount) | Absolute amount of active incorporated (wt. %) |
|---|---|---|
| 1-Hexanol | 75.0% | 18.8% |
| Trans-2-hexenal | 71.9% | 18.0% |
| Guaiacol | 68.7% | 17.2% |

Results are shown in Table 5. Incorporation of 1-hexanol, trans-2-hexenal, and guaiacol is shown as a percentage relative to the maximum theoretical incorporation based on the amount added to the coating solution, assuming no losses due to evaporation (25 wt. % of active), where it can be seen from the data that the PVOH based strips contain high levels of incorporated volatile liquid.

TABLE 6

Release kinetics of trans-2-hexenal.

| Time elapsed (hours) after strip inserted into GC vial at room temperature/95% RH | Concentration of trans-2-hexenal in headspace (ppm) |
|---|---|
| 0.17 | 350.60 |
| 0.70 | 589.45 |
| 1.25 | 1266.50 |
| 1.78 | 2036.63 |
| 2.33 | 3484.15 |
| 2.87 | 4541.25 |
| 3.42 | 6173.40 |
| 4.52 | 7357.28 |
| 17.77 | 6742.25 |

Analysis of Release of trans-2-hexenal or guaiacol from Coating into Headspace: A strip of approximately 13.6 cm$^2$ is cut from the middle of the coated PET sheet. The coating is peeled off the PET backer and then placed in a petri-dish in a fume-hood overnight to allow any residual non-encapsulated active to evaporate. A GC vial, 20 mL, with a screw-on septum-cap is prepared at 95% humidity by adding a mini plastic ultracentrifuge vial with the cap cut off containing approximately 0.20 g of saturated potassium nitrate (KNO$_3$) solution, with a few grains of solid KNO$_3$ added to maintain saturation. After allowing time (at least 2 hours) for the humidity in the vial to equilibrate, the strip of coating is added to the GC vial, and the vial immediately sealed. After allowing the desired amount of time for release of the active from the coating, a headspace sample is removed by syringe for injection into the GC column. The concentration in the Headspace is determined by comparing the GC Peak Area of the sample to the GC Peak Area of the headspace from a vial containing 0.5 mL of pure trans-2-hexenal, or guaiacol. The known vapor pressures of these compounds at room temperature can be used to calculate the saturated headspace concentration for these reference samples (8685, and 145 ppm (V/V) respectively).

Results for trans-2-hexenal are shown in Table 6, and results for guaiacol are shown in Table 7. It can be seen from the data that the strips containing trans-2-hexenal, and guaiacol, rapidly release the active compound to achieve headspace saturation levels in the GC vial on exposure to 95% relative humidity.

TABLE 7

Release kinetics of guaiacol.

| Time elapsed (hours) after strip inserted into GC vial at room temperature/95% RH | Concentration of guaiacol in headspace (ppm) |
|---|---|
| 0.62 | 76.17 |
| 1.2 | 81.90 |
| 1.75 | 80.20 |
| 3.52 | 82.55 |
| 23.75 | 89.52 |

What is claimed is:

1. A humidity-activated material in the form of a coating or film comprising:
   (a) a binder component; and
   (b) a volatile component dispersed in the binder component,
      wherein the binder component comprises polyvinyl alcohol and does not comprise cellulose, starch, gum, or polyethylene glycol;
      wherein the polyvinyl alcohol is at least 15% by weight of the material;
      wherein the volatile component has a boiling point between 40° C. and 300° C.;
      wherein the volatile component comprises a volatile compound selected from the group consisting of 1-hexanol, trans-2-hexanal and guaiacol;
      wherein the release of the volatile component from the binder component occurs between 60% and 100% relative humidity at room temperature; and
      wherein the volatile component is not encapsulated in a molecular encapsulating agent.

2. The material of claim 1, wherein the volatile component comprises guaiacol.

3. The material of claim 1, wherein the volatile component has a boiling point between 100° C. and 300° C.

4. The material of claim 1, wherein the release of the volatile component from the binder component occurs between 75% and 100% relative humidity at room temperature.

5. The material of claim 1, wherein the volatile component comprises solid precursors to the gaseous form of the volatile compound.

6. The material of claim 1, wherein the volatile component does not comprise a substance with a boiling point below 0° C.

7. The material of claim 5, wherein the volatile component does not comprise $CO_2$, $ClO_2$, or $SO_2$.

8. The material of claim 1, wherein the volatile component comprises liquid precursors to the gaseous form of the volatile compound.

9. The material of claim 1, wherein the polyvinyl alcohol is at least 25% by weight of the material.

10. The material of claim 1, wherein the polyvinyl alcohol is at about 15% to about 25% by weight of the material.

* * * * *